(12) United States Patent
Durand et al.

(10) Patent No.: US 9,636,239 B2
(45) Date of Patent: May 2, 2017

(54) SYSTEM AND METHOD FOR MAPPING ACTIVITY IN PERIPHERAL NERVES

(75) Inventors: Dominique M. Durand, Solon, OH (US); Brian Wodlinger, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1086 days.

(21) Appl. No.: 12/860,500

(22) Filed: Aug. 20, 2010

(65) Prior Publication Data

US 2011/0046506 A1    Feb. 24, 2011

Related U.S. Application Data

(60) Provisional application No. 61/235,591, filed on Aug. 20, 2009.

(51) Int. Cl.
| | |
|---|---|
| *A61B 5/05* | (2006.01) |
| *A61F 2/70* | (2006.01) |
| *A61F 2/72* | (2006.01) |
| *A61N 1/05* | (2006.01) |
| *A61B 5/04* | (2006.01) |
| *A61B 5/00* | (2006.01) |
| *A61N 1/36* | (2006.01) |

(52) U.S. Cl.
CPC ............ *A61F 2/72* (2013.01); *A61B 5/04001* (2013.01); *A61B 5/4041* (2013.01); *A61N 1/0551* (2013.01); *A61B 5/4064* (2013.01); *A61N 1/36003* (2013.01)

(58) Field of Classification Search
CPC . A61B 5/04001; A61B 5/4041; A61B 5/4064; A61B 5/076; A61F 2/72; A61N 1/0551; A61N 1/36103; A61N 1/0556; A61N 1/36003; A61N 1/36042; A61N 1/36067; A61N 1/08; A61N 2007/021
USPC ................... 600/372, 554; 607/2, 45, 47, 48
See application file for complete search history.

(56) References Cited

U.S. PATENT DOCUMENTS

| | | | | |
|---|---|---|---|---|
| 5,560,372 | A  * | 10/1996 | Cory ............................ | 600/554 |
| 6,171,239 | B1 * | 1/2001  | Humphrey .................... | 600/372 |
| 2003/0093129 | A1 * | 5/2003 | Nicolelis et al. .............. | 607/45 |

(Continued)

OTHER PUBLICATIONS

Struijk, J. J., Haugland, M. K., & Thomsen, M. (1996). Fascicle Selective Recording With a Nerve Cuff Electrode, 18th Annual International Conference of the IEEE Engineering in Medicine and Biology Society. (2.2.3: Peripheral Electrodes). 361-362.*

*Primary Examiner* — Christopher D Koharski
*Assistant Examiner* — Pamela M Bays
(74) *Attorney, Agent, or Firm* — Tarolli, Sundheim, Covell & Tummino LLP

(57) ABSTRACT

Systems and methods are provided for controlling an entity in response to activity in a peripheral nerve comprising a plurality of fascicles. A multicontact electrode assembly is configured to record activity from the peripheral nerve. A processing component includes a sensor mapping component configured to quantify activity associated with a proper subset of the plurality of fascicles, an evaluation component configured to determine an adjustment of the status of the controlled entity from the quantified activity of the proper subset of the plurality of fascicles, and a controller configured to provide a control signal, representing the adjustment of the status of the controlled entity, to the controlled entity.

9 Claims, 6 Drawing Sheets

(56) References Cited

U.S. PATENT DOCUMENTS

2003/0144710 A1* 7/2003 Haugland et al. ............ 607/48
2005/0288732 A1* 12/2005 Schuler ............ A61N 1/36042
607/48

* cited by examiner

SYSTEM AND METHOD FOR MAPPING ACTIVITY IN PERIPHERAL NERVES

RELATED APPLICATION

This application claims priority from U.S. Provisional Application No. 61/235,591, filed Aug. 20, 2009, the subject matter, which is incorporated herein by reference.

TECHNICAL FIELD

The present invention relates generally to the field of neural mapping, and more particularly to systems and methods for selectively recording sensed neural activity and controlling at least one entity based upon the sensed neural activity.

BACKGROUND OF THE INVENTION

Interest in the field of the natural control of human limbs using physiological signals has risen dramatically in the past 20 years due to the success of the brain-machine interface. Cortical signals carry significant information, but are difficult to access. The peripheral nerves of the body carry both command and sensory signals, and are far more accessible. While numerous studies have documented the selective stimulation properties of conventionally round electrodes, nerve cuff electrodes (i.e., transverse geometry), and even self-sizing electrodes, recording the activity levels from individual fascicles using these electrodes is still an unsolved problem.

Functional electrical stimulation (FES) can restore volitional motion to patients with neurological injuries or diseases using electrical stimulation of nerves innervating the muscles to be independently controlled. Developing a motion control algorithm for FES, however, is a challenging problem due to inherent complexities of musculoskeletal systems (e.g., highly nonlinear, strongly coupled, time-varying, time-delayed, and redundant properties) and the large number of channels required to activate the various muscles involved in the motion. Additionally, the localization and recovery of many signals poses a significant challenge due to the signal-to-noise ratio and the large number of fascicles.

SUMMARY OF THE INVENTION

In accordance with an aspect of the present invention, a system is provided for controlling an entity in response to activity in a peripheral nerve comprising a plurality of fascicles. A multicontact electrode assembly is configured to record activity from the peripheral nerve. A processing component includes a sensor mapping component configured to quantify activity associated with a proper subset of the plurality of fascicles, an evaluation component configured to determine an adjustment of the status of the controlled entity from the quantified activity of the proper subset of the plurality of fascicles, and a controller configured to provide a control signal, representing the adjustment of the status of the controlled entity, to the controlled entity.

In accordance with another aspect of the present invention, a method is provided for modeling a spatial sensitivity of a multicontact electrode assembly. The multicontact electrode assembly is affixed to a homogeneous test model. Respective sets of voltages are measured for a plurality of contacts associated with the multicontact electrode assembly. Each set of voltages represents the voltages at a plurality of locations on the test model when a known voltage is applied to its associated contact. A set of weights is determined from the sets of voltages for the plurality of contacts representing each location on the test model. A given set of weights represents the presence of an ideal point source at the location associated with the set of weights given the measured sets of voltages.

In accordance with a further aspect of the present invention, a method is provided for sensing activity within a peripheral nerve. A multi-contact electrode assembly is placed in contact with the peripheral nerve. A voltage is recorded at a plurality of contacts associated with the multicontact electrode assembly as a set of voltages. The set of voltages is multiplied by a transformation matrix to provide a voltage at each of plurality of locations on the peripheral nerve.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Unless otherwise defined, all technical terms used herein have the same meaning as commonly understood by one of ordinary skill in the art to which the present invention pertains.

In the context of the present invention, the terms "modulate" or "modulating" can refer to causing a change in neuronal activity, chemistry, and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "treating" can refer to therapeutically regulating, preventing, improving, alleviating the symptoms of, and/or reducing the effects of peripheral nerve dysfunction.

As used herein, the term "fascicle" can refer to a bundle of myelinated or non-myelinated nerve fibers surrounded by perineurium. A group of fascicles that make up a nerve are surrounded and held together by looser connective tissue called epineurium. Each fascicle can include one or more motor fiber (i.e., motor fascicle), sensory fiber (i.e., sensory fascicle), or sympathetic fiber in various numbers and combinations.

As used herein, the term "electrical communication" can refer to the ability of an electric field generated by a multi-contact electrode array to be transferred, or to have a neuromodulatory effect within and/or on at least one fascicle, nerve, nervous tissue and/or muscle.

As used herein, the term "peripheral nerve" can refer to any nerve that lies outside of the brain and spinal cord, i.e., the cranial nerves, spinal nerves, nerve plexuses, and their associated spinal and autonomic ganglia.

Figure 1:
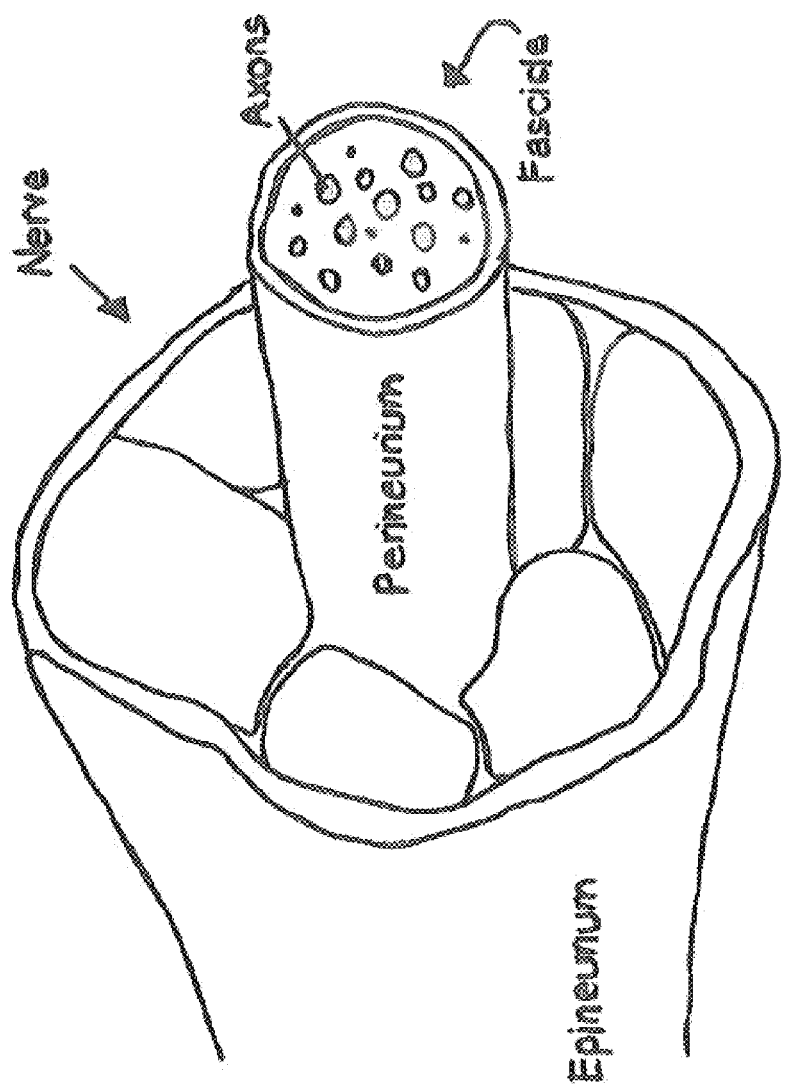
FIG. 1 is a schematic illustration showing the components of a peripheral nerve.

To assist the reader in understanding the present invention, FIG. 1 illustrates a nerve and various features to the level of individual axons. The nerve has an outer layer known as the epineurium that surrounds some fascicles. The epineurium acts as a connective tissue framework and sheath to bind together nerve bundles, known as fascicles. Each fascicle has an outermost connective tissue sheath known as the perineurium and each fascicle includes individual axons, which may be of more than one type. Depending on size, a fascicle may be referred to as a funiculus, and a fascicle may be considered as including more than one funiculi.

Figure 2:
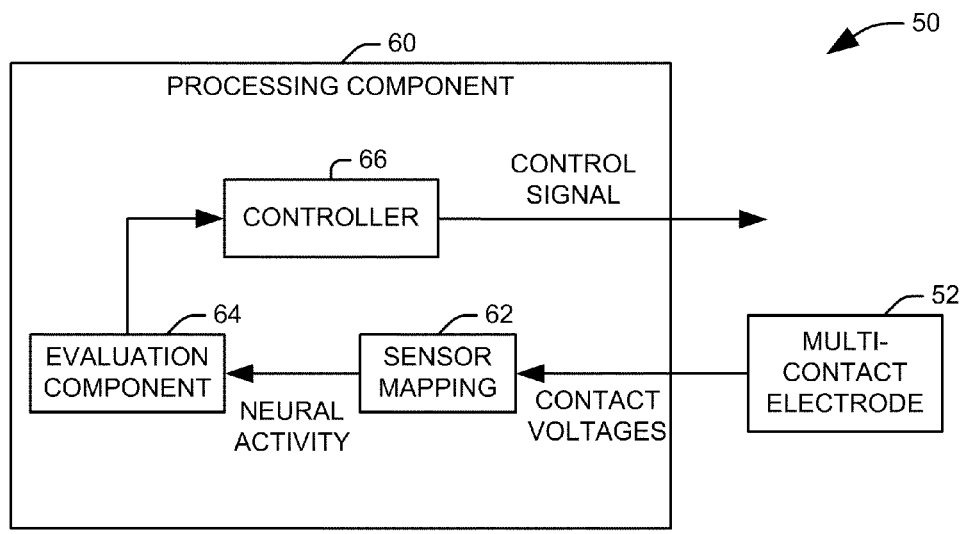
FIG. 2 illustrates a system for detecting activity of a target peripheral nerve in a subject and controlling an associated entity in accordance with an aspect of the present invention.

FIG. 2 illustrates a system 50 for detecting the activity of a target peripheral nerve in a subject and controlling at least one entity in response to the activity in accordance with an aspect of the present invention. The target peripheral nerve can include any nerve that lies outside of the central nervous system (i.e., the brain and spinal cord), such as a peripheral nerve located in an upper extremity or a lower extremity of the subject. It will be appreciated that the controlled entity can include the same nerve, a different nerve with a different electrode, an implanted device, such as a drug pump, an FES system (e.g., for muscular stimulation), an external prosthetic limb, or an external assistive device. In the illustrated system 50, a multi-contact electrode assembly 52 can be placed in electrical contact with the target peripheral nerve. The multi-contact electrode assembly can comprise a plurality of electrodes arranged in a desired configuration. The electrodes can be made of any one or combination of known electrically-conductive materials (e.g., a metal or metal alloy) and be at least partially encased in an electrically-insulative material. The entire surface area of the electrodes may be conductive or, alternatively, only a portion of the surface area of the electrodes may be conductive. The electrodes may have any shape and size, including, for example, disc-shaped, a triangular shape, a rectangular shape, an ovoid shape, and/or a band-like shape (e.g., a split band configuration).

One example of a multi-contact electrode assembly that can be contacted with the target peripheral nerve is a flat interface nerve electrode (FINE), which is disclosed in U.S. Pat. No. 6,456,866, the entirety of which is hereby incorporated by reference. The FINE comprises a pair of beams closed at the ends to form a flattened, rectangular opening. Electrical contacts or electrodes are embedded within the beam walls and, when the FINE is placed around a nerve, the beams are deformed around the nerve. Compared to an electrode with a circular geometry, the flat geometry of the FINE offers several advantages. For example, the circumference of the flattened geometry is larger for the same cross-sectional area, allowing more electrical contacts to be placed around the nerve. Additionally, the maximum distance from any axon to an electrical contact on the FINE is smaller than for a circular electrode, effectively moving central tissue to the surface of the nerve. Thus, the flat geometry aligns the nerve fascicles to increase selectivity and access to every fascicle.

In accordance with an aspect of the present invention, the multi-contact electrode assembly 52 can be configured to communicate with a processing component 60 that receives and processes information from the electrode assembly. It will be appreciated that the processing component 60 can be implemented as software operating on a general purpose processor, dedicated hardware, programmable logic devices, or some combination of these elements. Further, while the processing component 60 is illustrated as an integral unit, it will be appreciated that the various functions performed by the processing component can be separated into discrete modules that are spatially remote but in communication within one another. Accordingly, the processing component 60 can be implemented either within the body of the subject, external to the body, or some combination of both.

The processing component 60 comprises a sensor mapping element 62 that maps activity detected at the multi-contact electrode onto a spatial distribution representing the peripheral nerve. For example, the sensor mapping element 62 can multiply a vector representing the detected voltage by a transformation matrix representing the spatial sensitivity of the multi-contact electrode to estimate the spatial distribution of the neural activity. By mapping the detected activity onto a higher resolution spatial distribution, it is possible to acquire information about the activity of at least one sensor fascicle and at least one motor fascicle of the target peripheral nerve. Further, it is possible to exclude at least one fascicle within the nerve from the acquired information, such that the at least sensor or motor fascicle represents a proper subset of the fascicles in the nerve. Given an appropriate distribution of electrodes, the sensor mapping element 62 can generate a 2.5- or 3-dimensional mapping as a spatial representation of the target peripheral nerve activity (e.g., nerve conduction or action potential propagation) to provide a temporal component to the spatial representation of the neural activity, from which a magnitude of fascicular signals, the direction of those signals, and/or their speed can be determined.

One or more of the determined spatial mapping, the amplitude of the fascicular signals, the speed of the fascicular signals, and the direction of the fascicular signals can be provided to an evaluation component 64 configured to determine an appropriate adjustment of the status of the controlled entity from the activity at the mapped fascicles. In one implementation, the evaluation component 64 is configured to determine the difference between a desired limb position or muscle force and a limb position or muscle force indicated by the fascicular signals and determine a therapeutic adjustment for a peripheral nerve associated with the muscle based on the determined difference. To this end, the evaluation component 64 can include a feedback controller (e.g., a PID controller) that compares the indicated position to the determined position and outputs a desired correction. In one implementation, the evaluation component 64 can further comprise a feed forward controller (e.g., implemented as a neural network) to provide a correction to the measured error based on the desired value.

Alternatively, the evaluation component 64 can determine an appropriate control signal for a medical device, such as a prosthesis, implanted therapeutic device, or external assistance device. In this instance, the evaluation component 64 can determine an appropriate adjustment in the status of the medical device based upon the sensed neural activity. For example, where the device is a drug pump, the sensed neural activity can indicate a need for an adjustment of a delivery rate of the pump. Alternatively, where the device is a prosthetic device, the sensed neural activity can indicate a desire to generate a specific movement or movements in the prosthetic device.

The determined adjustment is provided to a 66 configured to provide a corresponding control signal to the controlled entity. For example, in a functional electrical stimulation (FES) application, the controller 66 can include an inverse steady state controller (ISSC) that can be trained empirically for each patient to translate the desired correction for a given physiological parameter (e.g., muscle force or limb position) into a therapeutic stimulation pattern that will produce the desired correction. The control signal can comprise electrical energy supplied from an internal or external power source in either a periodic or continuous manner. The control signal can be delivered to, for example via the electrodes of the multi-contact electrode array or via another mechanism implanted within or affixed to the body of the subject, in an amount and for a time sufficient to modulate at least one of limb position and muscle force in the subject. Where the controlled entity is an external assistance device, implanted medical device, or prosthesis, the controller 66 can include a formatting function that encodes the desired adjustment to the function of the controlled device in a format recognizable to the device.

Figure 3:
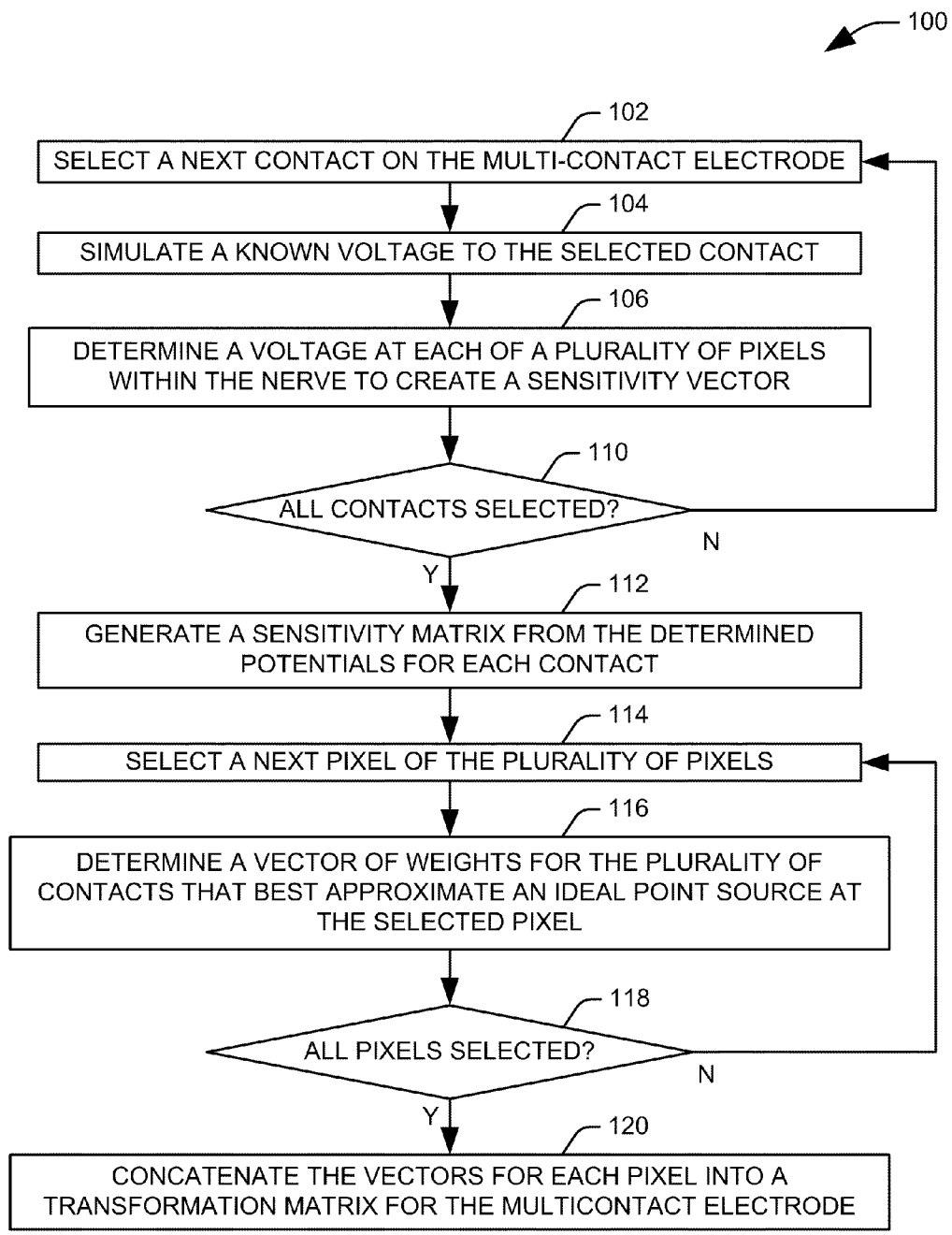
FIG. 3 illustrates a methodology for configuring a multi-contact electrode apparatus in accordance with an aspect of the present invention.
Figure 4:
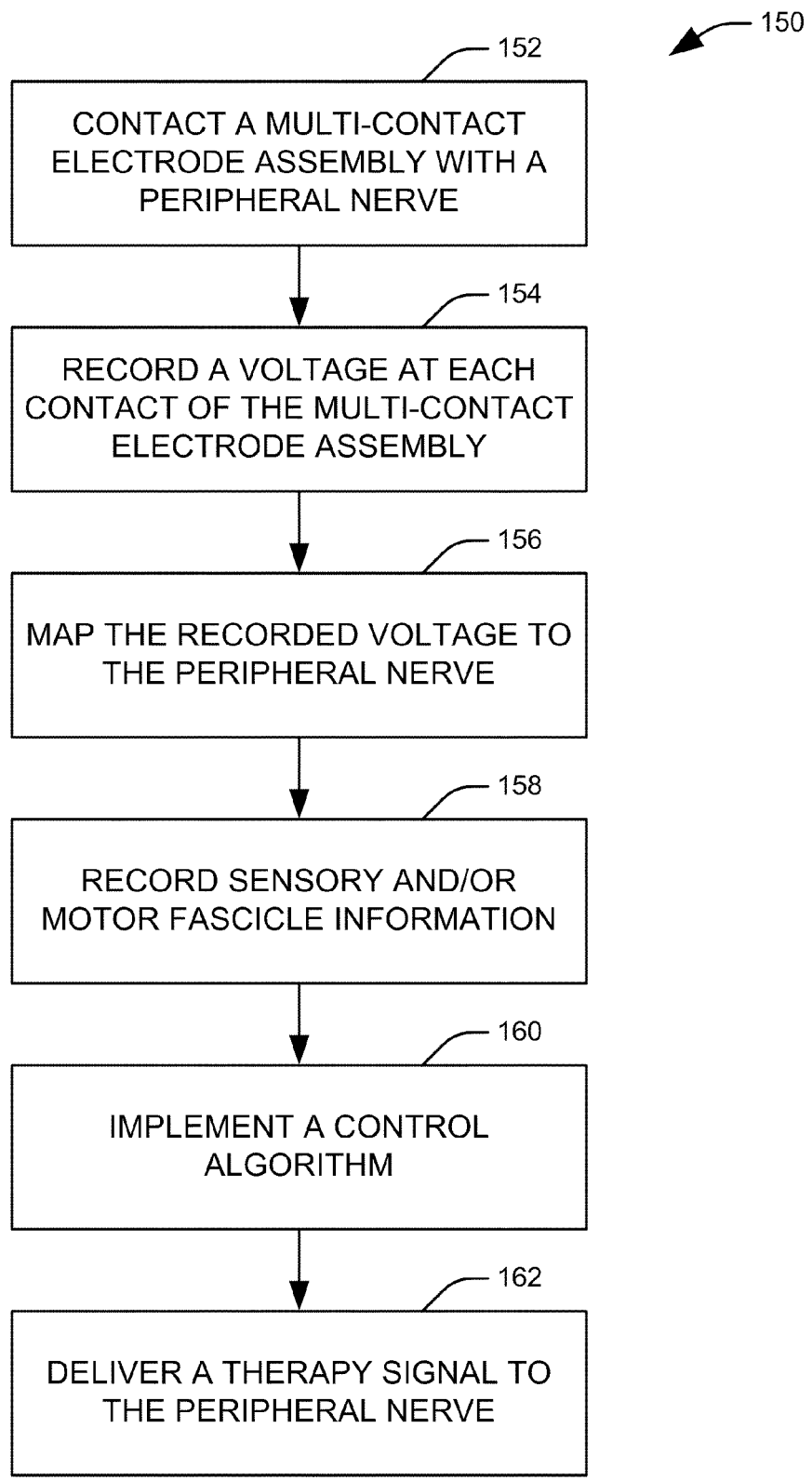
FIG. 4 is a process flow diagram illustrating a method for modulating the activity of a peripheral nerve in a subject according to one aspect of the present invention.

In view of the foregoing structural and functional features described above, methodologies in accordance with various aspects of the present invention will be better appreciated with reference to FIGS. 3 and 4. While, for purposes of simplicity of explanation, the methodologies of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 3 illustrates a methodology 100 for configuring a multi-contact electrode apparatus in accordance with an aspect of the present invention. The illustrated methodology 100 calculates a set of weights for each recording contact on a cuff electrode apparatus in order to map the sensitivity of the recording contacts to electric impulses within a peripheral nerve. To this end, the performance of the electrode apparatus can be evaluated using a homogeneous test model containing no a priori assumptions on the geometry and conductance of the peripheral nerve. Specifically, the nerve can be modeled as a rectangular epineurium in a very large saline volume conductor. The potential within the nerve given the applied voltage can be estimated at each of a plurality of pixels within the model to determine the sensitivity of the nerve to a voltage at each contact, and a least squares optimization process can be used to find an optimal set of weights for the contacts to represent the response at a given pixel.

At step 102, a position associated with a first contact from the multi-contact electrode is selected, and a known voltage is simulated at the selected contact at step 104. In one implementation, the applied voltage is one mV. At step 106, the voltage induced within the nerve by the simulated voltage is determined at each of a plurality of locations, or pixels, within the nerve. The voltage can be recorded as an m×1 vector, in which m is the number of pixels at which the voltage is recorded. It will be appreciated that each recorded vector estimates the sensitivity of the nerve to a voltage at the selected contact and, due to electromagnetic reciprocity, the sensitivity of the selected contact to voltage at each pixel within the nerve. At step 110, it is determined if all of the contacts had been evaluated. If not (N), the methodology 100 returns to step 102 to select a next contact from the multi-contact electrode. Once all of the contacts have been evaluated (Y), the methodology advances to step 112.

At step 112, a sensitivity matrix is generated from the recorded vectors for each of the plurality of contacts to represent the sensitivity of the multi-contact electrode to voltage at various points within the nerve. For example, the vectors for the plurality of contacts can be concatenated to form an m×n matrix, when n is the number of contacts on the multi-contact electrode. At step 114, a first pixel of the plurality of pixels defined within the nerve is selected. At step 116, a set of weights for the plurality of contacts is determined that best represents the presence of an ideal point source at the selected pixel given the measured sensitivity of the contacts to voltage within the nerve. In one implementation, the weights can be calculated via a least squared optimization process, wherein a vector of weights, $t_i$, for a given pixel, i, of the plurality of pixels is calculated to minimize the deviation of the product of the sensitivity matrix, S, and the vector of weights from a delta function, $\delta_i$, representing a maximum sensitivity at the selected pixel and no response elsewhere. The optimization problem can thus be represented as:

$$St_i = \delta_i \qquad \text{Eq. 1}$$

To facilitate efficient computation of the weights, the sensitivity matrix can be represented as a QR decomposition of the matrix, and the optimal solution to the least squares optimization problem can be represented as:

$$t_i = R^{-1}(Q^T \delta_i) \qquad \text{Eq. 2}$$

Given the properties of the delta function, $\delta_i$, this reduces to:

$$t_i = R^{-1} q_i \qquad \text{Eq. 3}$$

where $q_i$ is the $i^{th}$ row of the orthogonal matrix Q.

Once the optimal set of weights have been calculated, they can be normalized, such that:

$$t'_i = \frac{t_i}{\|St_i\|} \qquad \text{Eq. 4}$$

At step 118, it is determined if a set of weights has been determined for each pixel. If not (N), the methodology 100 returns to step 114 to select a next pixel from the plurality of pixels. Once a vector of weights has been produced for each pixel (Y), the methodology advances to step 120, where a transformation matrix is produced from the vector of weights provided for each pixel. In one implementation, the transformation matrix represents a concatenation of the 1×n weight vectors for each of the m pixels, such that the final transformation matrix is an m×n matrix configured to map a set of n potentials from the multi-contact electrode into localized valued for each of the m pixels. Accordingly, the weights comprising the transformation matrix can be used to separate signals originating from different spatial locations, such as signals from separate fascicles.

FIG. 4 illustrates another aspect of the present invention comprising a method 150 for modulating the activity of a peripheral nerve in a subject. The peripheral nerve can include any nerve that lies outside of the central nervous system (i.e., the brain and spinal cord), such as a peripheral nerve located in an upper extremity or a lower extremity of the subject. Non-limiting examples of peripheral nerves can include the radial nerve, the median nerve, the ulnar nerve, the femoral nerve, the obturator nerve, the sciatic nerve, the popliteal nerve, the tibial nerve, the peroneal nerve, and the vagus nerve.

Identification of the peripheral nerve depends upon the health of the subject. Most of the time, a loss in control of an extremity or limb due to disease or trauma will indicate which peripheral nerve(s) should be targeted. In a subject suffering from drop foot, for example, the peripheral nerve can include the peroneal or sciatic nerves. Alternatively, in a subject with a leg injury that results in the inability to extend the knee, the peripheral nerve can include the femoral nerve. Other applications of the present invention include natural control of artificial limbs for subjects with amputated limbs and restoration of function in subjects with stroke or paralyzed limbs.

As shown in FIG. 4, the method 150 includes contacting a multi-contact electrode assembly with the peripheral nerve at step 152. Using a minimally invasive surgical technique, the multi-contact electrode assembly is contacted with or to the peripheral nerve so that multiple rows of electrical contacts (i.e., electrodes) are located transverse to the nerve. For example, the multi-contact electrode assembly can be implanted on the peripheral nerve under direct visualization and/or using image guidance (e.g., MRI, CT, ultrasound, fluoroscopy, etc.). In an example of the present invention, a FINE can be implanted on a peripheral nerve by surgically accessing the peripheral nerve and slipping the open side of the FINE over the nerve. The FINE is opened to completely encircle the nerve, at which point the two open and opposing ends of the FINE are connected together (e.g., using an O-ring or suture). The FINE encircles the peripheral nerve and gently and non-invasively applies a defined exterior force over time to redefine the geometry of the nerve, such as by flattening.

The multi-contact electrode assembly can be in communication with a power source for providing electrical energy to the electrodes. For example, one or more electrical leads can be connected between one or more of the electrodes and the power source. Alternatively, the multi-contact electrode assembly can self-contained unit, e.g., including a rechargeable battery, such as the BION Microstimulator device (Boston Scientific, Natick, Mass.). Additionally or optionally, the multi-contact electrode assembly may be in communication with the power source via wireless mechanism (e.g., RFID).

Electrical energy can be delivered to the electrodes using a variety of internal, passive, or active energy delivery sources. The energy source may include, for example, radio frequency (RF) energy, X-ray energy, microwave energy, acoustic or ultrasound energy such as focused ultrasound or high intensity focused ultrasound energy, light energy, electric field energy, magnetic field energy, biological tissue energy harvesting techniques, combinations of the same, or the like.

After contacting the multi-contact electrode assembly with the peripheral nerve, a sensing algorithm is implemented to acquire information about the activity of at least one sensory fascicle and at least one motor fascicle of the peripheral nerve. As discussed above, the sensing algorithm is used to generate a 2.5- or 3-dimensional image of the peripheral nerve activity (e.g., nerve conduction or action potential propagation), from which fascicular signals, the direction of those signals, and/or their speed can be determined. Based at least on part from the acquired information, the location and activity of individual sensory and motor fascicles can be determined. To this end, a voltage at each of the contacts on the multi-contact electrode assembly is measured at step 154. The measured voltages are then mapped onto the peripheral nerve at step 156 to provide a spatial distribution of the activity within the nerve. For example, the spatial sensitivity of the multi-contact electrode can be represented as a transformation matrix, which can be applied to a vector comprising the recorded voltages to estimate a spatial distribution of the nerve activity. By mapping the contact voltages to a higher resolution spatial distribution, it is possible to detect the magnitude and direction of activity within individual nerve fascicles with substantial accuracy.

At step 158, the information acquired by the sensing algorithm is recorded on a computer readable medium. The computer readable medium can comprise any storage or transmission medium that participates in providing instructions and/or data to the system for execution and/or processing. Examples of storage media can include floppy disks, magnetic tape, CD-ROM, a hard disk drive, a ROM or integrated circuit, a magneto-optical disk, or a computer readable card, such as a PCMCIA card, and the like.

Either during or after acquisition and recordation of the information at step 158, the control algorithm is implemented (step 160). As discussed above, implementation of the control algorithm generates a control signal based on the recorded information. The control signal specifies at least one of limb position and muscle force in the subject. For example, the control signal can provide a gauge of the grip force or slip of an object being held by the subject. The control signal is then recorded using a computer readable medium.

At step 162, a therapy signal (as discussed above) is delivered to the peripheral nerve based on the recorded control signal. For example, the control signal can be used to generate a therapeutic stimulation pattern and monitor reflex activity in the target peripheral nerve. The therapy signal can comprise electrical energy supplied from a power source in either a periodic or continuous manner. Electrical energy can be delivered to the electrodes of the multi-contact electrode assembly in an amount and for a time sufficient to modulate at least one of limb position and muscle force in the subject.

For example, the therapy signal can be delivered to the electrodes of the multi-contact electrode assembly in an amount and for a time sufficient to provide substantially natural control of at least one dysfunctional limb or extremity. In a subject suffering from drop foot, for instance, the therapy signal can be delivered to the electrodes of a multi-contact electrode assembly implanted on the sciatic nerve to restore normal nerve-to-muscle signals in the subject's leg and foot, effectively lifting the foot at the appropriate time during the gait cycle. It will be appreciated that the method 150 can also be used to assist a subject in operating a prosthetic limb.

Figure 5:
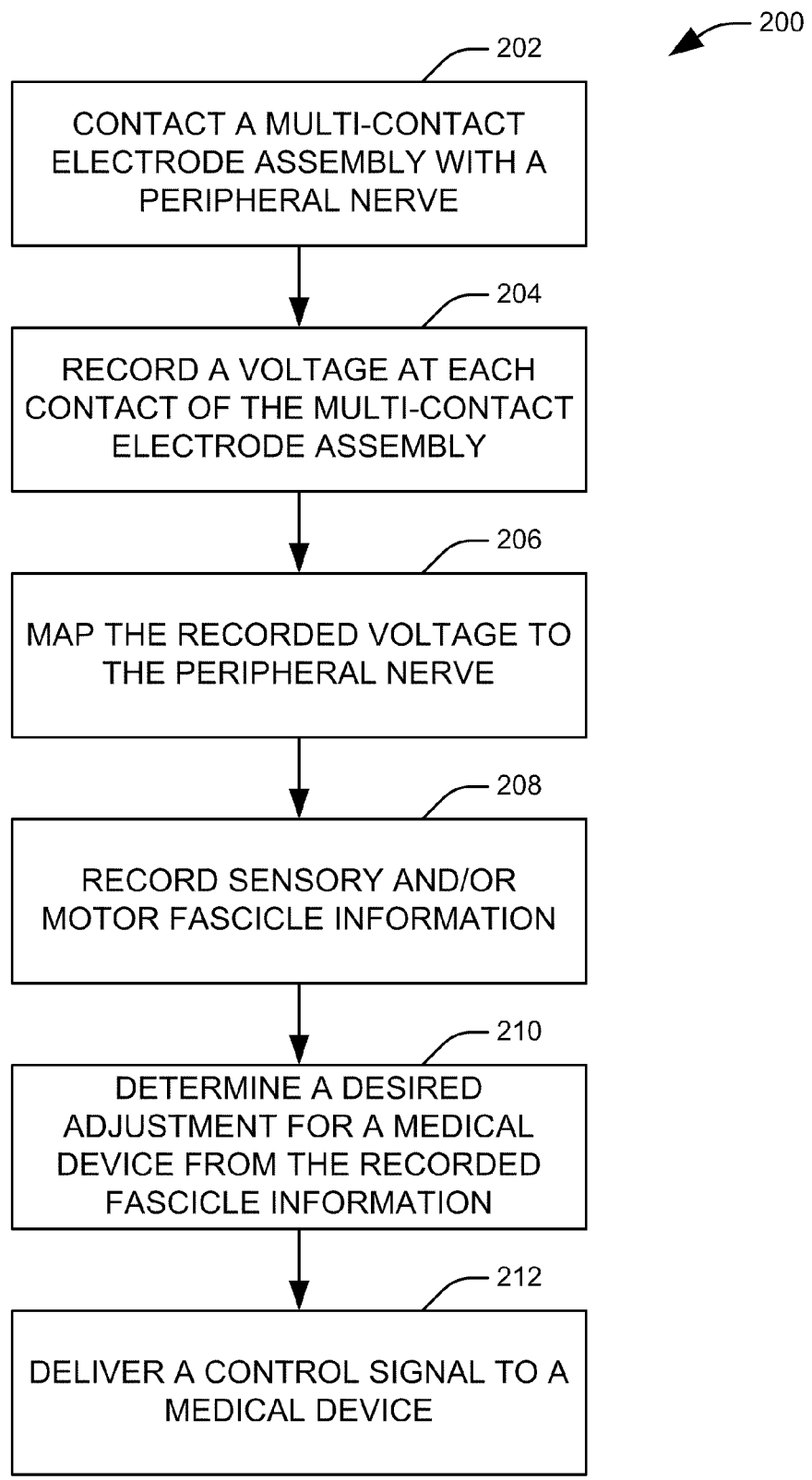
FIG. 5 illustrates a method for controlling a medical device according to sensed neural activity in a peripheral nerve in accordance with an aspect of the present invention.

FIG. 5 illustrates a method 200 for controlling a medical device according to sensed neural activity in a peripheral nerve in accordance with an aspect of the present invention. The target peripheral nerve can include any nerve that lies outside of the central nervous system. The controlled medical device can include one or more of an external assistance device, and medical implant (e.g., drug pump or FES electrode), or a prosthetic device.

As shown in FIG. 5, the method 200 includes contacting a multi-contact electrode assembly with the target peripheral nerve at step 202. After contacting the multi-contact electrode assembly with the target peripheral nerve, a sensing algorithm is implemented to acquire information about the activity of at least one sensor fascicle and at least one motor fascicle of the target peripheral nerve. As discussed above, the sensing algorithm is used to generate a 2.5- or 3-dimensional image of the target peripheral nerve activity (e.g., nerve conduction or action potential propagation), from which fascicular signals, the direction of those signals, and/or their speed can be determined. Based at least on part from the acquired information, the location and activity of individual sensory and motor fascicles can be determined. To this end, a voltage at each of the contacts on the multi-contact electrode assembly is measured at step 204. The measured voltages are then mapped onto the peripheral nerve at step 206 to provide a spatial distribution of the activity within the nerve. For example, the spatial sensitivity of the multi-contact electrode can be represented as a transformation matrix, which can be applied to a vector comprising the recorded voltages to estimate a spatial distribution of the nerve activity. By mapping the contact voltages to a higher resolution spatial distribution, it is possible to detect the magnitude and direction of activity within individual nerve fascicles with substantial accuracy.

At step 208, the information acquired by the sensing algorithm is recorded on a computer readable medium. The computer readable medium can comprise any storage or transmission medium that participates in providing instructions and/or data to the system for execution and/or processing. Examples of storage media can include floppy disks, magnetic tape, CD-ROM, a hard disk drive, a ROM or integrated circuit, a magneto-optical disk, or a computer readable card, such as a PCMCIA card, and the like.

The recorded information is then provided to an evaluation component, and a desired adjustment to the function of the medical device is determined from the recorded information at 210. In determining the desired adjustment, the neural activity recorded from the peripheral nerve is interpreted to associate with the neural activity with one or more scalar values or event classes. For example, where the device is an external assistance device or a prosthetic device, the evaluation component can classify the neural activity into one or more event classes associated with respective commands for the device by the user. In this implementation, an appropriate training process can be performed to facilitate the identification. Alternatively, the evaluation component can identify at least one physiological parameter associated with the neural activity, and the desired adjustment can be a change in the function of an implanted device to adjust the physiological parameter.

At 212, a control algorithm generates a control signal based on the desired adjustment to the function of the medical device. The control signal can comprise a digital or analog signal that instructs the medical device to adjust a status or function of the device according to the recorded neural activity. In one implementation, the control algorithm includes a data interface that generates a command for the medical device in an appropriate format.

It will be appreciated that the transformation matrix provides a substantially accurate approximation of a filter, represented by the calculated set of weights, for each location in the nerve cross-section. It will be appreciated, however, that there are differences between the model used to generate the transformation matrix and the nerve cross-section. Specifically, the sources are not points, as the activity in a given fascicle can be represented across a number of individual pixels.

In accordance with an aspect of the present invention, the determined transformation matrix can be used as a basis from which multiple filters can be linearly combined to take into account the size and shape of the source of the neural activity, as well as particular locations with interference. To this end, the filter calculation is determined not only on the pixel with strongest signal, but the entire image generated by the transformation matrix. Accordingly, the filters for every pixel are weighted by value of the source image at every pixel, to create an overall filter for the fascicle. This places more emphasis on locations where the source is stronger, and provides some spatial averaging to reduce noise.

Figure 6:
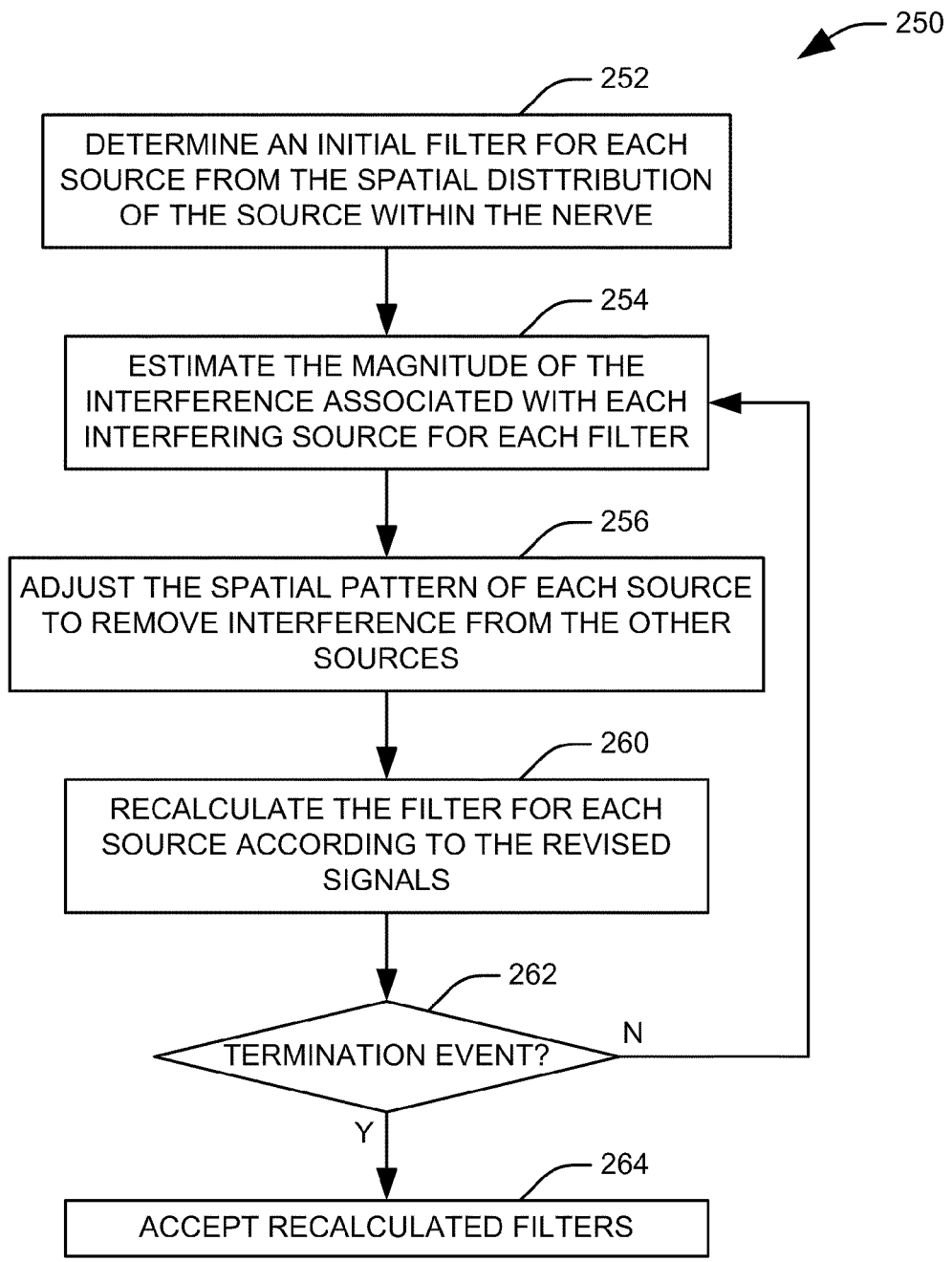
FIG. 6 illustrates another aspect of the present invention comprising a method for generating a filter associated with a signal source to reduce cross-talk from interfering sources.

FIG. 6 illustrates another aspect of the present invention comprising a method 250 for producing a filter associated with a source to reduce cross-talk from interfering sources Specifically, a custom weighting, referred to herein as a filter, of the sensor activity recorded at the multicontact electrode can be determined for a given source of neural activity, such as a fascicle within the nerve. The illustrated methodology 250 focuses on determining filters for two sources, for the purpose of example, but this methodology can be applied to any number of signal sources within the peripheral nerve.

At 252, an initial filter is determined for an each of a plurality of signal sources, represented here as a first source, T, and a second source, P, according to a spatial distribution of the source within the nerve. The initial filter can be determined as from a sensitivity matrix, S, representing the sensitivity of the multicontact electrode assembly to voltage within the nerve. The initial filter for each source can thus be calculated as:

$$T_{filter} = T_{loc}{}^T \times S \quad P_{filter} = P_{loc}{}^T \times S \qquad \text{Eq. 5}$$

wherein $T_{loc}$ is a vector representing the spatial distribution of the first source as a mapping of the activity observed from the first source onto a plurality of locations within the nerve, and $P_{loc}$ is a vector representing the spatial distribution of the second source representing a mapping of the activity observed from the second source onto the plurality of locations.

At 254, a magnitude of the interference with each signal associated with each source caused by each other source can be estimated. In the current example, the interference at the first source given a signal at the second source, P→T, and the interference at the second source given a signal at the first source, T→P, can be estimated as:

$$T \to P = (S \times P_{filter})^T T_{loc} \quad P \to T = (S \times T_{filter})^T P_{loc} \qquad \text{Eq. 6}$$

At 256, the spatial distribution of each source is adjusted to remove interference associated with the other sources. For example, the interference with a given source associated with each of a plurality of other sources can be determined, multiplied by their respective spatial distributions, and summed to provide a correction. The correction is subtracted from the existing spatial distribution for the source to provide a revised spatial distribution. This can be repeated for each source to provide corresponding revised distributions for each source. For the two source example, the revised spatial distributions are calculated as:

$$T_{loc} = T_{loc} - (P \to T) \times (P_{loc} - T_{loc}) \quad P_{loc} = P_{loc} - (T \to P) \times (T_{loc} - P_{loc}) \qquad \text{Eq. 7}$$

At 260, the filters are recalculated, as shown above in 252, using the revised mappings. At 262, it is determined if a termination event has occurred. For example, the termination event can include a determination that the correction produced at 256 fell below a threshold magnitude or the performance of a maximum number of iterations. If a termination event has not occurred (N), the methodology returns to 254 to produce a new estimate of the interference caused by the source. If a termination event has occurred (Y), the recalculated filtered are accepted at 264, and the methodology terminates.

Figure 7:
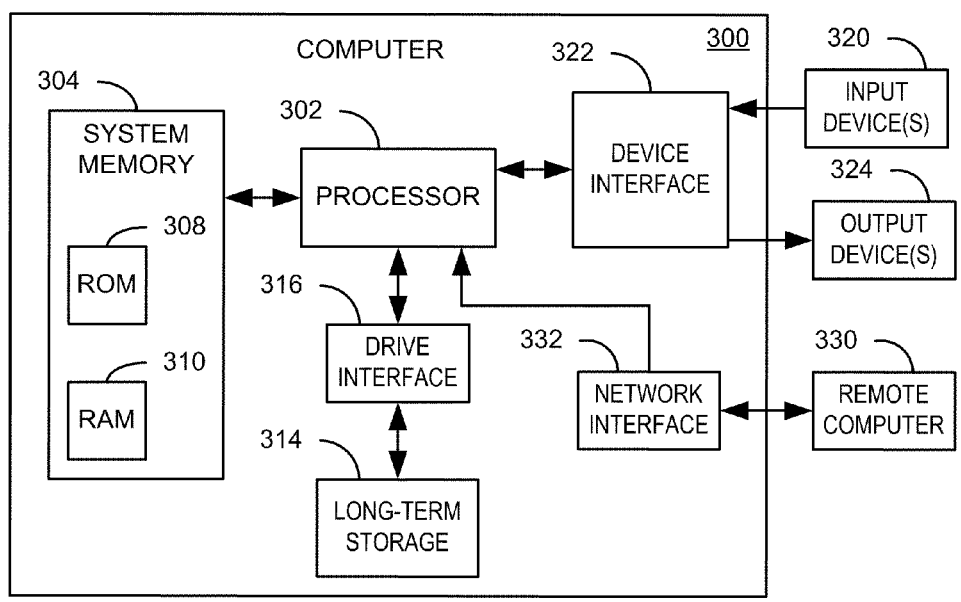
FIG. 7 illustrates a computer system that can be employed to implement systems and methods described herein.

FIG. 7 illustrates a computer system 300 that can be employed to implement systems and methods described herein, such as based on computer executable instructions running on the computer system. The computer system 300 can be implemented on one or more general purpose networked computer systems, embedded computer systems, routers, switches, server devices, client devices, various intermediate devices/nodes and/or stand alone computer systems. Additionally, the computer system 300 can be implemented as part of the computer-aided engineering (CAE) tool running computer executable instructions to perform a method as described herein.

The computer system 300 includes a processor 302 and a system memory 304. Dual microprocessors and other multi-processor architectures can also be utilized as the processor 302. The processor 302 and system memory 304 can be coupled by any of several types of bus structures, including a memory bus or memory controller, a peripheral bus, and a local bus using any of a variety of bus architectures. The system memory 304 includes read only memory (ROM) 308 and random access memory (RAM) 310. A basic input/output system (BIOS) can reside in the ROM 308, generally containing the basic routines that help to transfer information between elements within the computer system 300, such as a reset or power-up.

The computer system 300 can include one or more types of long-term data storage 314, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 302 by a drive interface 316. The long-term storage components 314 provide nonvolatile storage of data, data structures, and computer-executable instructions for the computer system 300. A number of program modules may also be stored in one or more of the drives as well as in the RAM 310, including an operating system, one or more application programs, other program modules, and program data.

A user may enter commands and information into the computer system 300 through one or more input devices 320, such as a keyboard or a pointing device (e.g., a mouse). These and other input devices are often connected to the processor 302 through a device interface 322. For example, the input devices can be connected to the system bus by one or several parallel ports, a serial port or a universal serial bus (USB). One or more output device(s) 324, such as a visual display device or printer, can also be connected to the processor 302 via the device interface 322.

The computer system 300 may operate in a networked environment using logical connections (e.g., a local area network (LAN) or wide area network (WAN) to one or more remote computers 330. A given remote computer 330 may be a workstation, a computer system, a router, a peer device or other common network node, and typically includes many or all of the elements described relative to the computer system 300. The computer system 300 can communicate with the remote computers 330 via a network interface 332, such as a wired or wireless network interface card or modem. In a networked environment, application programs and program data depicted relative to the computer system 300, or portions thereof, may be stored in memory associated with the remote computers 330.

From the above description of the invention, those skilled in the art will perceive improvements, changes and modifications. Such improvements, changes and modifications are within the skill of the art and are intended to be covered by the appended claims.

Having described the invention, we claim:

1. A system comprising:
a multicontact electrode assembly configured to record voltage activity from a peripheral nerve, wherein each contact of the multicontact electrode assembly is associated with a weight representing a presence of an ideal point source at a location associated with the respective contact, wherein a set of the weights are concentrating into a transformation matrix representing a spatial sensitivity of the peripheral nerve;
a processing component comprising:
a sensor mapping component configured to map the voltage activity detected at the multicontact electrode onto a spatial distribution representing the peripheral nerve based on the transformation matrix to determine a relative voltage activity of each ideal point source;
an evaluation component configured to classify the relative voltage activity into an event class associated with a respective command for medical device based on at least one of the ideal point sources; and
a controller component configured to provide a control signal to the medical device, wherein the control signal is determined based on the event class associated with the respective command for the medical device,
wherein the medical device changes a function based by adjusting at least one physical parameter based on the control signal.

2. The system of claim 1, the sensor mapping component being configured to map the voltage activity at the peripheral nerve as a representation comprising a temporal component, such that at least one of the direction and the speed of the voltage activity is determined.

3. The system of claim 1, the sensor mapping component being configured to represent the activity measured at the multi-contact electrode assembly as a vector of voltages and multiply the vector of voltages by the transformation matrix.

4. The system of claim 3, the sensor mapping component being configured to construct a filter associated with at least one fascicle as a linear combination of a plurality of vectors from the transformation matrix.

5. The system of claim 1, the sensor mapping component being configured to quantify activity from at least two fascicles and determine a custom filter for a given fascicle from the quantified activity for the at least two fascicles.

6. The system of claim 1, the medical device comprising at least one of an external assistive device, and implanted medical device, and a prosthetic limb, the controller comprising an interface for providing the control signal to the medical device.

7. The system of claim 1, and the controller being configured to produce a stimulation pattern for the medical device, wherein the medical device comprises the multicontact electrode assembly.

8. The system of claim 7, wherein the evaluation component is configured to monitor reflex activity in the peripheral nerve in response to the stimulation pattern.

9. The system of claim 1, the controller being configured to produce a therapeutic stimulation pattern for a second multicontact electrode assembly within the medical device.

* * * * *